United States Patent [19]

Schoots

[11] Patent Number: 4,704,113
[45] Date of Patent: Nov. 3, 1987

[54] DRESSING

[75] Inventor: Peter J. Schoots, Walpole, Mass.

[73] Assignee: The Kendall Company, Walpole, Mass.

[21] Appl. No.: 791,320

[22] Filed: Oct. 25, 1985

Related U.S. Application Data

[63] Continuation of Ser. No. 491,014, May 3, 1983, abandoned.

[51] Int. Cl.⁴ ............................................. A61F 13/16
[52] U.S. Cl. .................................... 604/379; 604/370; 604/378; 128/156
[58] Field of Search ............... 604/379, 380, 378, 370; 128/155, 156; 428/152; 162/111

[56] References Cited

U.S. PATENT DOCUMENTS

| | | | |
|---|---|---|---|
| 2,508,214 | 5/1950 | Biederman | 604/378 |
| 3,260,778 | 7/1966 | Walton | 264/282 |
| 3,485,706 | 12/1969 | Evans | 428/134 |
| 3,971,381 | 7/1976 | Gibson | 604/378 |
| 4,093,765 | 6/1978 | Schmidt | 604/378 |
| 4,208,459 | 6/1980 | Becker et al. | 604/380 |
| 4,214,582 | 7/1980 | Patel | 128/156 |

Primary Examiner—C. Fred Rosenbaum
Assistant Examiner—Sherri E. Vinyard
Attorney, Agent, or Firm—Hale and Dorr

[57] ABSTRACT

A dressing comprising a textile-like nonwoven fabric characterized in that the fibers comprise a blend of fibers including a percentage (preferably from about 15 to about 60 percent) of thermoplastic fibers, and the fabric is compacted (preferably micro-creped at an overfeed not less than 10 percent and typically in the range of about 20 to about 30 percent and at a drum temperature of greater than about 250 degrees F.) subsequent to hydro-entangling the fibers. prior to compacting, the fabric typically has a weight in the range of about 20 to 60 grams per square yard. After compacting, the fabric has an absorptive capacity and a liquid transfer both of which are greater than the absorptive capacity and liquid transfer of a hydro-entangled fabric of the same weight and fiber blend which has not been compacted.

18 Claims, 7 Drawing Figures

U.S. Patent Nov. 3, 1987 Sheet 1 of 4 4,704,113
FIG 1
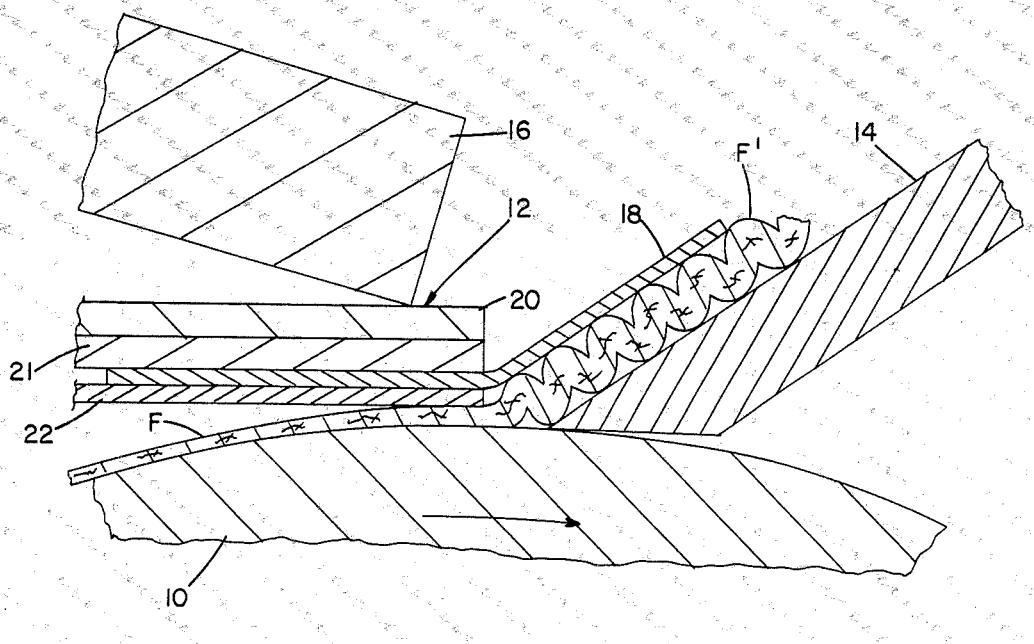
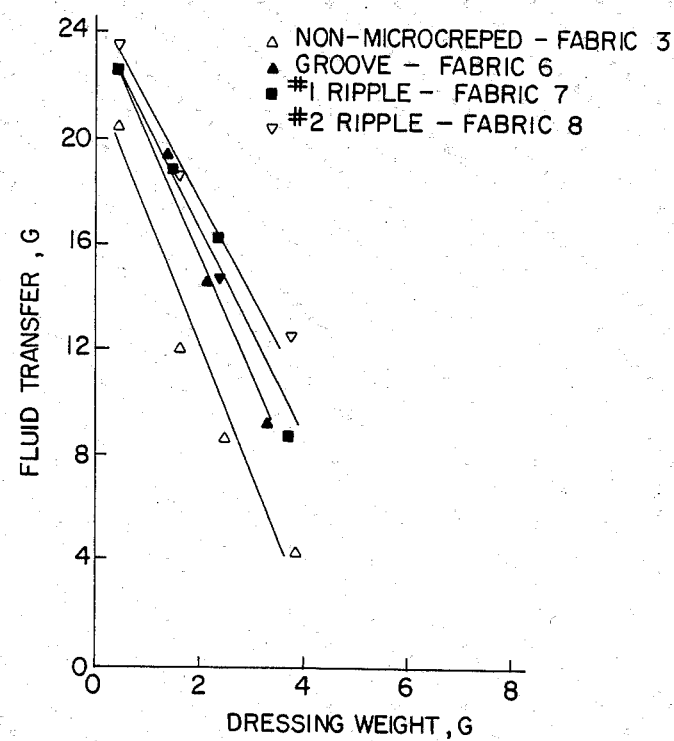
FIG 6

FIG 2
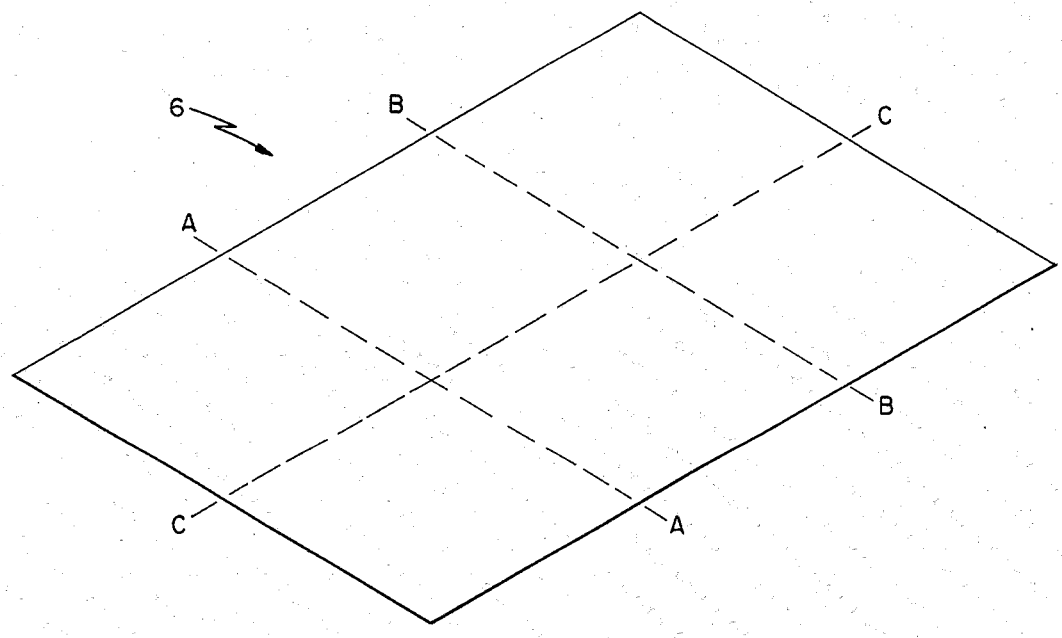
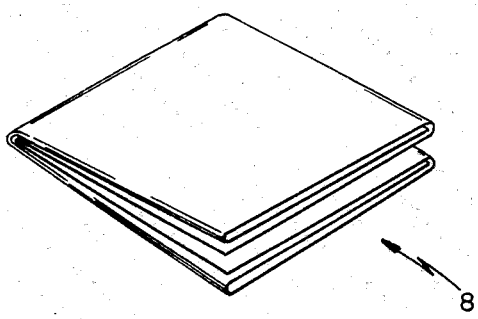
FIG 3

DRESSING

This is a continuation of application Ser. No. 491,014, filed May 3, 1983 now abandoned.

BACKGROUND OF THE INVENTION

This invention relates to hospital dressings and sponges and, more particularly, to hospital dressings and sponges of hydro-entangled fabric.

Two important functional properties of a surgical dressing are its absorptive capacity, i.e., its ability to absorb and hold liquid, and its liquid transfer properties, i.e., its ability to wick and transfer exudate of the wound away from the wound site. The former is of principal importance when the dressing is used as a sponge for cleaning and wiping wounds and instruments; the latter when it is used as a dressing or to pack a wound.

One type of surgical dressing currently marketed is made of woven gauze which has excellent wicking and fluid transfer properties. However, when used alone for wiping or cleaning, gauze has a relatively poor absorptive capacity.

A second type of surgical dressing currently available is made of hydro-entangled fibers. This type of dressing has a good absorptive capacity, but relatively poor fluid transfer characteristics.

Prior to the present invention, the understanding and experience of workers in the field was that an increase in absorbency of a dressing is accompanied by a decrease in its liquid transfer properties.

SUMMARY OF THE INVENTION

The principal object of the present invention is to provide a surgical dressing that has improved both absorptive capacity and liquid transfer properties.

It has been discovered that the absorptive capacity and liquid transfer properties of dressings made from homogeneous compacted non-woven fibers, particularly micro-compacted, hydro-entangled fabrics, unexpectedly are both superior to the corresponding properties of hydro-entangled fabrics of the same weight and fiber blend that have not been compacted.

The invention thus features a dressing comprising a textile-like nonwoven fabric characterized in that the fibers comprise a blend of fibers including a percentage (preferably from about 15 to about 60 percent) of thermoplastic fibers, and the fabric is compacted (preferably micro-creped at an overfeed not less than 10 percent and typically in the range of about 20 to about 30 percent and at a drum temperature of greater than about 250 degrees F.) subsequent to mechanically-entangling the fibers. Prior to compacting, the fabric typically has a weight in the range of about 20 to 60 grams per square yard. After compacting, the fabric has an absorptive capacity and a liquid transfer both of which are greater than the absorptive capacity and liquid transfer of a hydro-entangled fabric of the same weight and fiber blend which has not been compacted.

BRIEF DESCRIPTION OF THE DRAWINGS

FIG. 1 is a simplified plan view of portions of a machine used to compact the hydro-entangled fabric used in the practice of the present invention.

FIG. 2 is a perspective view of fabric prior to folding into a dressing.

FIG. 3 is a perspective view of a dressing embodying the present invention.

FIGS. 4–6 are graphs illustrating properties of dressings embodying the invention.

DESCRIPTION OF PREFERRED EMBODIMENTS

Figure 4:
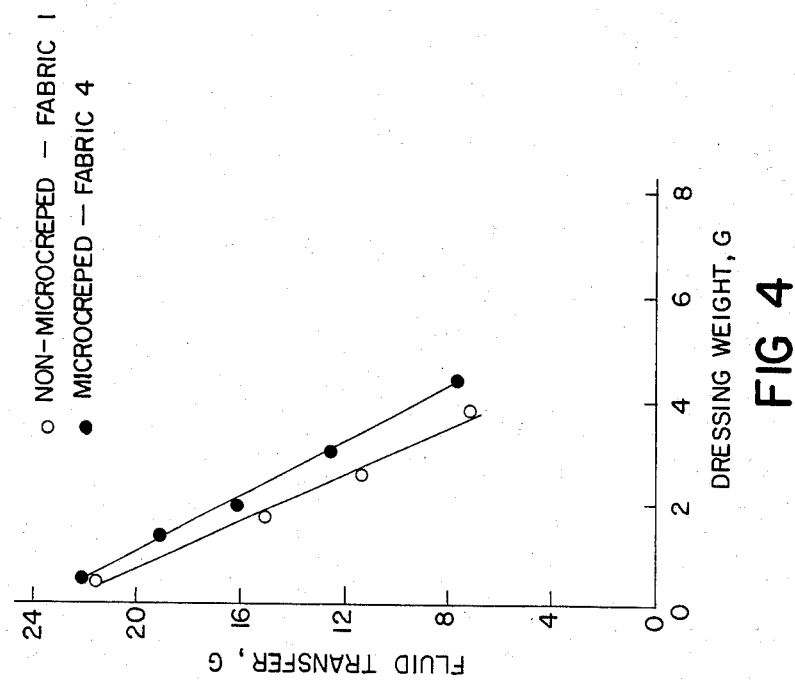

The unique dressings of the present invention incorporate non-woven textile fabrics, preferably made in accordance with the teachings of U.S. Pat. No. 3,485,706 issued to F. S. Evans on Dec. 26, 1969 and hereinafter referred to as "hydro-entangled" fabric. As described therein, those fabrics comprise fibers locked into place by fiber interaction to provide a strong cohesive structure which maintains its structural integrity without the need for adhesive binders or filament fusing. The fabrics have a pattern of entangled fiber regions of higher area density (weight per unit area) than the average area density of the fabrics as a whole and there are interconnecting fibers which extend between the dense entangled regions and are randomly entangled with each other in the dense entangled regions. As is described in the aforementioned patent to Evans, the entanglement is accomplished by first preparing a loose layer of fibers and then passing the layer through an entangler where it is treated with liquid, jetted at a pressure of at leaast 200 psig, from one or more rows of small orifices, to convert the layer into non-woven fabrics.

In accordance with the present invention a blend of cellulosic fibers (preferably rayon) and thermoplastic fibers (preferably polyester) is formed into a mechanically-entangled fabric by passing the loose fiber layer through an entangler having four rows (i.e., manifolds) of jets, under the following conditions:

| | |
|---|---|
| Entangler speed | 50 feet per minute |
| Winder speed | 52 feet per minute |
| Jet size | 5 mil diameter |
| Number of jets/inch | 60 (Cross-Machine Direction) |
| Screen design | 22 holes per inch (MD) by 24 holes per inch (CD) |
| Wire diameter | 20 mil round warp wire 17.55 mil round shute wire |
| Manifold Pressures | |
| #1 | 300 psi |
| #2 | 600 psi |
| #3 | 1000 psi |
| #4 | 1400 psi |
| Drying Can Temperatures Stack No. | |
| 1 | 250° F. |
| 2 | 250° F. |
| 3 | ambient |

The hydro-entangled non-woven fabric so made is then compacted, preferably in accordance with the teachings of one or more of U.S. Pat. Nos. 3,260,778 issued to R. R. Walton on July 12, 1966, 3,810,280 issued to R. R. Walton and George E. Munchbach on May 14, 1974, and 4,080,385 issued to Thomas D. Packard on May 23, 1980. Hereinafter, the machines which compact a fabric are referred to as "microcrepers," the compacting procedure as "micro-creping," and fabrics that have been so compacted or micro-creped as "micro-creped fabrics."

Microcrepers for producing such micro-creped fabrics are available from Bird Machine Company of Walpole, Mass.; and are sold by it under the trademark "Micrex."

The manner in which the aforementioned microcrepers, and the apparatus disclosed in the aforementioned patents, micro-crepe fabrics is shown in somewhat simplied form in FIG. 1. As there shown, a travelling length of fabric F is driven forward by a heated rotary drum 10 into the nip between the drum 10 and a presser assembly 12. The drum may have either a grooved surface (as shown in U.S. Pat. No. 4,080,385) or a generally cylindrical surface (e.g., a cylindrical surface which may be somewhat roughened as shown in some embodiments of U.S. Pat. No. 3,810,280). The temperature to which the drum surface is heated depends on the particular fabric being micro-creped. It is typically heated to above 250 degrees F., preferably to about 300 degrees F. and, if polyethylene fibers are used, typically to not more than about 310 degrees F. The presser assembly 12 forces the fabric toward the surface of the drum 10 at a point close to vertical alignment with the drum axis. A retarder 14 engages the fabric F as it passes the presser 12, and both retards the fabric and diverts it away from the surface of drum 10 at an acute angle. As shown, the forward end of the presser assembly 12 is urged towards drum 10 by a pressure applying member 16. A spring plate 18, sandwiched between upper plates 20, 21 and lower plate 22 of presser assembly 12, extends beyond plates 20, 21 and 22 so that it overlies the adjacent end of retarder 14, engages the face of the fabric F opposite that engaging retarder 14, and forms a passage for the fabric which converges in the direction of fabric travel.

As shown, the combined action of the drum 10, presser assembly 12 and retarder 14 imparts micropleats or the like to the fabric, squeezing or compacting it in such a way as to cause the fabric to be rearranged into a repeating series of wave-like undulations extending substantially throughout its length and running across the width of the fabric. The heat from the drum softens the thermoplastic fibers in the fabric so that, when it is cooled, the fabric will maintain its micropleated, wave-like form; and the thus micro-creped fabric, designated F', is passed to a rewind roll (not shown). The extent to which the peripheral speed of drum 10 exceeds the speed at which the micro-creped fabric F' is taken up on the rewind roll, expressed as a percentage of the take-up speed, is referred to as the "overfeed." Thus, for example, if the peripheral speed of the drum is 60 feet per minute and the fabric is taken up at 50 feet per minute, the overfeed is 20 percent. In the practice of the present invention, it has been found that the overfeed generally should not be less than about 10 percent, and typically should be in the range of about 20 to about 30 percent, depending on the particular drum, presser assembly and temperature employed. As will be seen, the overfeed used with the preferred groove pattern is 30 percent.

According to the preferred practice of the present invention, the hydro-entangled non-woven fabric is micro-creped under the following conditions:
Overfeed: 20-30 percent.
Temperature: 300° F.
Drum speed: 50-75 feet per minute.

As indicated previously, the drum of the microcreper may be either grooved or may have a generally cylindrical outer surface. The selection of the drum, and of the pressure assembly used to press the fabric on the hot drum, depend on the desired texture of the final fabric. In the preferred practice of the invention, the drum has a grooved surface of the type disclosed in aforesaid U.S. Pat. No. 4,090,385 and the presser assembly includes two upper plates (i.e., plates 20, 21) of 0.020 inch thick spring steel, a lower plate (i.e., plate 22) of 0.010 inch thick coated steel of the type sold by Microfin, Inc. of Providence, R.I. under the tradename "Microlube", and a spring plate (i.e., plate 18) of 0.003 inch thick spring steel.

The fabric of the preferred embodiment is made from a 50/50 blend of rayon fibers (1½ denier, 1 9/16 inch staple length) and high crimp polyester fibers (DuPont FO8 fiber, 1½ denier, 1.5 inch staple length). The particular fiber denier, staple length and crimp are not critical. For example, a high crimp fiber will produce a thicker but somewhat weaker fabric than will a low crimp fiber; and under some circumstances this may be desired. Polypropylene fibers (e.g., Hercules T123 fibers) may be used in lieu of polyester, in which event the drum of the microcreper on which the hydro-entangled fabric is micro-creped typically will be maintained at a somewhat lower temperature. Regardless of what thermoplastic fiber is employed, the percent thereof in the blend may be varied—the governing factors being, on the one hand, that there be sufficient thermoplastic fiber to insure that the fabric will maintain its undulating, micro-creped form and, on the other hand, that the fabric as a whole will be sufficiently hydrophilic for its intended use as a hospital sponge or dressing. Blends typically used will include from about fifteen to about sixty percent thermoplastic fiber. The remaining fibers typically will be cellulosic, although a percentage of non-cellulosic fibers such as acrylic fibers may be included also. The weight of the hydro-entangled fabric, typically, will be in the range of about 20 to about 60 grams per square yard (gsy).

In accordance with the present invention, the hydro-entangled, micro-crèped fabric may be incorporated into a surgical sponge having a plurality of plies. FIG. 2 illustrates a single rectangular sheet 10 of hydro-entangled fabric which may be folded to produce the six-ply sponge 12 shown in FIG. 3. The sheet 10 is first folded along lines A—A and B—B, which extend in the machine direction and divide the fabric generally in thirds. The final product, sponge 12, is achieved by folding transversly, along line C—C which extends in the cross-direction and divides the fabric generally in half. Sponge 12 is 4 in.×4 in. in size.

The fabric of the present invention may, of course, be used to make dressings and sponges having any desired number of plies, or may be used in a single-ply dressing if so desired.

Two important properties of a dressing are its absorptive capacity, i.e., the amount of liquid which the dressing will absorb per gram of fabric in the dressing, and its fluid transfer properties, i.e., the extent to which the dressing, when used as a primary dressing placed next to a wound or other fluid source, will transfer fluid through its thickness to a secondary dressing.

Typically, absorptive capacity is measured by completely submerging a pre-weighed dressing in water, removing it from the water and permitting it to drain, and then weighing to determine the weight of water retained in the dressing. The absorptive capacity (in grams of water per gram of dressing fabric) is calculated by dividing the weight of water retained by the weight of the dry dressing. Typical tests for measuring such capacity include ASTM - D1117 Sec. 5.

As indicated above, fluid transfer is important in wound management systems that comprise both a primary dressing and a secondary dressing, the primary dressing being placed next to the wound so that it will transfer fluid to the secondary dressing which is desired to absorb and hold most of the fluid. Typically, fluid transfer is expressed in terms of the percent of fluid presented to the primary dressing that is transfered vertically through it to the secondary dressing, and is measured by applying a known quantity of fluid (e.g., 25 ml) to the bottom of the primary dressing and then weighing the secondary dressing to determine how much of the liquid has been transferred to it.

A system for so measuring the fluid transfer is shown in FIG. 8 and, as illustrated, includes a test table 50 mounted above a base plate 52 on which is mounted an on-off valve 54. Centered on the top surface of the test table is a 5/32 inch diameter fluid delivery orifice 56. A 60 milliliter 1 3/16 in. ID., 5⅛ in. high, calibrated burett 58 is placed vertically on a stand next to the test table with its stopcock 60 7½ in. above the top of the test table. Flexible tubes 62, 64 connect the base of the burrett to valve 54 and the valve to orifice 56 (e.g., tube 64 is pressed into orifice 56 with the top of the tube extending slightly above the table top).

A flat 147 gram plexiglass pressure plate 66 is provided for insuring intimate contact between the fluid outlet orifice 56 and the dressing(s) being tested.

In testing, stopcock 60 is adjusted to attain a 13–15 ml/minute flow from an unobstructed fluid orifice. When it has been set, everything is shut off and dried, and burrett 58 is filled. Two pre-weighed primary dressings and a secondary dressing are then placed on the test table 50, with the primary dressings on the table top, one-third overlapped with the overlapped portions centered over fluid delivery orifice 56. The secondary dressing is placed on the primary dressing, and the pressure plate 66 is placed on top of the secondary dressing.

The on-off valve 54 is then opened to allow free flow of fluid therethrough. When 25 ml of fluid have been dispensed, the on-off valve immediately is closed. The wet primary and secondary dressings are then weighed separately. As indicated above, the amount of fluid transferred through the primary dressing to the secondary dressing determines the fluid transfer, which typically is expressed in either total weight (e.g., grams) or as a percentage of the total fluid applied to the bottom of the primary dressing from the orifice 56.

Dressings of the present invention exhibit properties which are totally unexpected when contrasted with prior dressings. Specifically, it has been found that both the absorptive capacity and the liquid transfer properties of the hydro-entangled fabric are improved by micro-creping. Heretofore it was generally believed, and was the experience of workers in the field, that an increase in absorptive capacity is accompanied by a decrease in liquid transfer properties.

With respect to absorptive capacity, it has been found that micro-creping hydro-entangled fabric increases absorptive capacity as much as about 40 percent (compared to hydro-entangled fabric of the same weight and blend that has not been micro-creped) while at the same time causing an increase of almost 10 percent in liquid transfer. This means, surprisingly, that the fabric of the present invention can be used to produce either superior wound dressings (where transfer properties are important) or superior hospital sponges (where absorbant capacity is important).

To further illustrate the advantages of the invention, the following examples are given.

In each of the following examples, the fabrics used are hydro-entangled fabrics produced according to the conditions discussed above. The fabrics identified as "microcreped" are microcreped by Bird Machine Company of Walpole, Mass., using its microprosessors, under one of the three following sets of conditions:

1. Groove Pattern, 30% overfeed, 300° F., Groove Drum;
2. #1 Ripple Pattern, 20% overfeed, 300° F., Cylindrical Drum; or,
3. #2 Ripple Pattern, 20% overfeed, 300° F., Cylindrical Drum.

In all examples, the samples are die-cut and hand-folded into 4"×4" dressings of either 1, 4, 6 or 9 ply. All samples are allowed to condition for a minimum of 1 hour at 72° F. and 50% relative humidity. In all examples, deionized water is used as the test fluid.

EXAMPLE I

Sample dressings having varying number of plies are prepared from the following different fabrics:

Fabric 1—hydro-entangled fabric made from a blend of 65% rayon fibers and 35% polypropylene fibers (R/PP, 65/35) and having a single ply weight of 33.8 gsy (grams per square yard).

Fabric 2—hydro-entangled fabric made from a blend of 65% rayon fibers and 35% polypropylene fibers and having a single ply weight of 55.6 gsy.

Fabric 3—hydro-entangled fabric made from a blend of 50% rayon fibers and 50% polyester fibers (R/PET, 50/50) and having a single ply weight of 34.5 gsy.

Fabric 4—hydro-entangled fabric made from a blend of 65% rayon fibers and 35% polypropylene fibers and micro-creped using the groove pattern, the fabric after micro-creping having a single ply weight of 38.4 gsy.

Fabric 5—hydro-entangled fabric made from a blend of 65% rayon fibers and 35% polypropylene fibers and micro-creped using the groove pattern, the fabric after micro-creping having a single ply weight of 47.9 gsy.

Fabric 6—hydro-entangled fabric made from a blend of 50% rayon fibers and 50% polyester fibers and micro-creped using the groove pattern, the fabric after micro-creping having a single ply weight of 29.5 gsy.

Fabric 7—hydro-entangled fabric made from a blend of 50% rayon fibers and 50% polyester fibers and micro-creped using the #1 ripple pattern, the fabric after micro-creping having a single ply weight of 30.2 gsy.

Fabric 8—hydro-entangled fabric made from a blend of 50% rayon fibers and 50% polyester fibers and micro-creped using the #2 ripple pattern, the fabric after micro-creping having a single ply weight of 31.6 gsy.

The absorptive capacity of sample dressings made from each of the above fabrics are tested, with the results shown in Table I.

TABLE I

| Absorptive Capacity | | | |
|---|---|---|---|
| Non-Micro-creped | | Micro-creped | |
| Dressings | Capacity, g/g | Dressings | Capacity, g/g |
| Fabric 1, 6 ply (R/PP, 33.8 gsy) | 12.4 | Fabric 4, 6 ply (R/PP, 38.4 gsy, |  14.8 |

TABLE I-continued

| Non-Micro-creped | | Micro-creped | |
|---|---|---|---|
| Dressings | Capacity, g/g | Dressings | Capacity, g/g |
| | | Groove Pattern) | |
| Fabric 2, 4 ply (R/PP, 55.6 gsy) | 9.3 | Fabric 5, 4 ply (R/PP, 47.9 gsy, Groove Pattern) | 13.0 |
| Fabric 3, 6 ply (R/PET, 34.5 gsy) | 12.9 | Fabric 6, 6 ply (R/PET, 29.5 gsy, Groove Pattern) | 17.6 |
| | | Fabric 7, 6 ply (R/PET, 30.2 gsy, #1 Ripple Pattern) | 14.1 |
| | | Fabric 8, 6 ply (R/PET, 31.6 gsy, #2 Ripple Pattern) | 14.2 |

Absorptive Capacity

Dressings made from micro-creped fabrics show a consistently higher absorptive capacity than do dressings made from non-micro-creped fabrics of approximately the same weight (gsy), for both rayon/polyester and rayon/polypropylene fiber blends. The dressings made with R/PET fabrics micro-creped with the groove pattern have higher absorptive capacity than the dressings made with R/PP fabrics micro-creped with the same pattern. It is postulated that this is caused by the fact that the polyester fiber in the R/PET fabrics has a better heat setting capability than does the polypropylene fibers, which makes the micro-creped fabrics including polyester fiber more resistant to collapsing when wet. The groove pattern (at 30% overfeed) enhances absorptive capacity of the R/PET dressings to a greater extent than do the #1 or #2 ripple patterns (at 20% overfeed).

EXAMPLE II

The fluid transfer of sample dressings made from each of the fabrics listed in Example I are tested, with the results shown in Table II.

TABLE II

Fluid Transfer

| NON-MICRO-CREPED | | | | | MICROCREPED | | | |
|---|---|---|---|---|---|---|---|---|
| Dressing | Ply | Sponge Weight, g | Transfer* g | % | Dressing | Ply | Sponge Weight, g | Transfer* g | % |
| Fabric 1 | 1 | .42 | 21.6 | 66.4 | Fabric 4 | 1 | .46 | 22.0 | 88.5 |
| (R/PP, | 4 | 1.65 | 15.0 | 59.5 | (R/PP, | 4 | 1.87 | 16.2 | 65.1 |
| 33.8 gsy) | 6 | 2.50 | 11.5 | 46.3 | 38.4 gsy | 6 | 2.90 | 12.6 | 50.6 |
| | 9 | 3.73 | 7.3 | 29.2 | Groove) | 9 | 4.29 | 7.8 | 31.5 |
| Fabric 2 | 1 | .69 | 18.9 | 76.4 | Fabric 5 | 1 | .56 | 20.6 | 83.3 |
| (R/PP, | 4 | 2.77 | 8.7 | 35.0 | (R/PP, | 4 | 2.32 | 12.5 | 50.1 |
| 55.6 gsy) | 6 | 4.14 | 4.3 | 17.4 | 47.9 gsy, | 6 | 3.67 | 7.6 | 30.4 |
| | 9 | 6.24 | .77 | 3.1 | Groove) | 9 | 5.30 | 3.2 | 10.9 |
| Fabric 3 | 1 | .41 | 20.4 | 83.7 | Fabric 6 | 1 | .37 | 22.5 | 90.6 |
| (R/PET, | 4 | 1.69 | 12.0 | 48.5 | (R/PET, | 4 | 1.39 | 19.2 | 76.6 |
| 34.5 gsy) | 6 | 2.51 | 8.8 | 35.2 | 29.5 gsy | 6 | 2.16 | 14.6 | 58.0 |
| | 9 | 3.88 | 4.3 | 17.4 | Groove) | 9 | 3.32 | 9.2 | 35.7 |
| | | | | | Fabric 7 | 1 | .37 | 22.3 | 89.9 |
| | | | | | (R/PET, | 4 | 1.51 | 18.8 | 75.7 |
| | | | | | 30.9 gsy | 6 | 2.34 | 16.2 | 65.3 |
| | | | | | #1 Ripple) | 9 | 3.63 | 9.7 | 37.7 |
| | | | | | Fabric 8 | 1 | .40 | 23.5 | 94.6 |
| | | | | | (R/PET, | 4 | 1.57 | 18.6 | 75.0 |
| | | | | | 31.6 gsy | 6 | 2.34 | 14.6 | 58.4 |
| | | | | | #2 Ripple) | 9 | 5.75 | 12.4 | 43.7 |

*Transfer is based on total test fluid used, approximately 25 ml.

Figure 5:
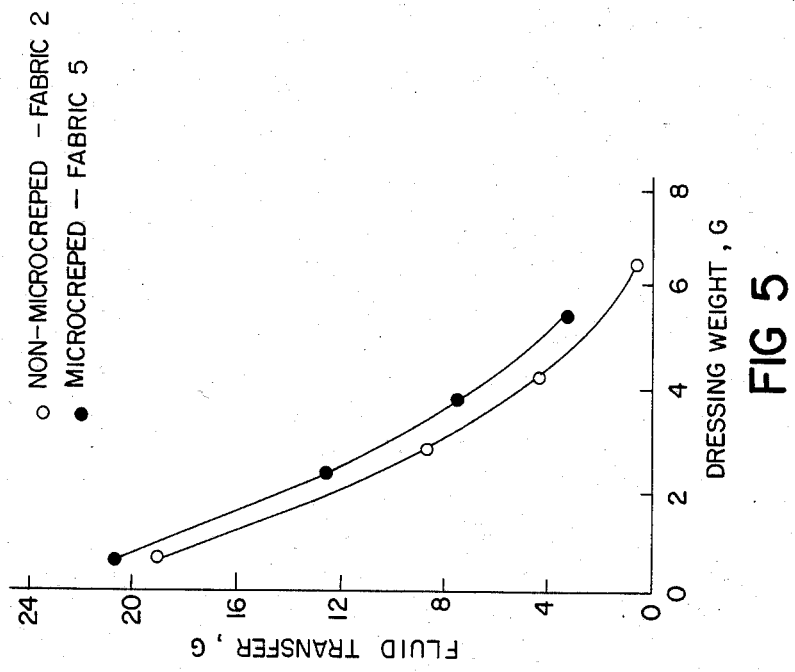
Figure 7:
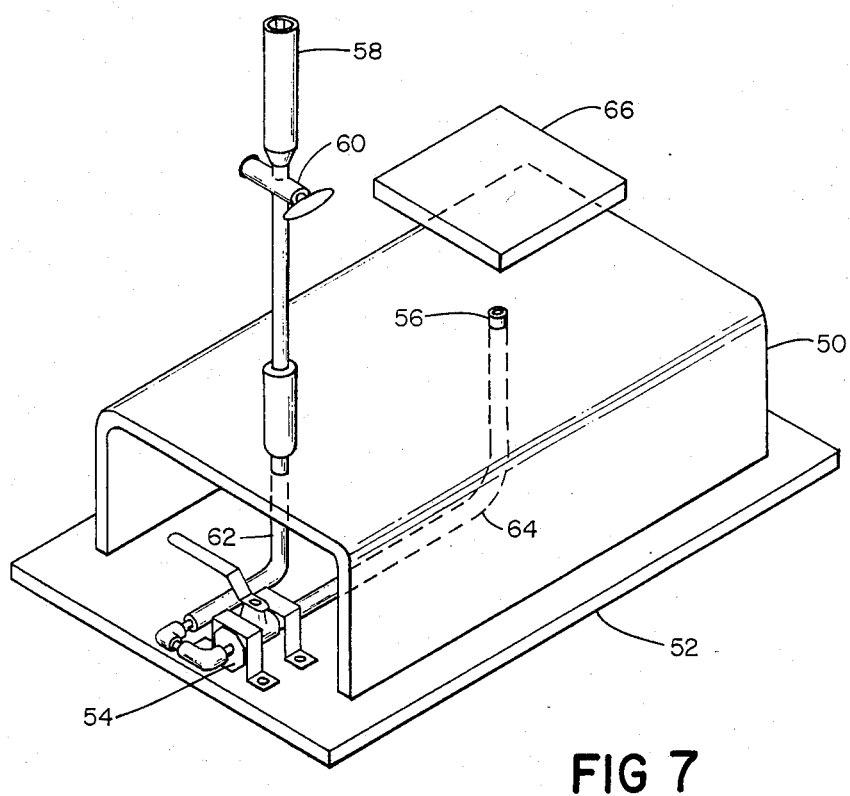
FIG. 7 is a view of liquid transfer test apparatus.

FIGS. 4-6 of the drawings graphically set forth data from Table II, and illustrate the effect on fluid transfer resulting from micro-creping hydro-entangled fabrics, FIG. 4 illustrates the effect on relatively light-weight R/PET fabrics (fabrics 1 and 4); FIG. 5, the effect on heavier R/PET fabrics (fabrics 2 and 5); and FIG. 6, on R/PP fabrics (fabrics 3, 6, 7 and 8). As shown in these drawings, all dressings made of micro-creped hydroentangled fabrics show a higher fluid transfer than do dressings made of nonmicro-creped hydroentangled fabric of the same blend and approximately the same dressing weight. The heavier basis weight dressings made from R/PP fabrics have a lower transfer than do the light basis weight dressings of the same blend, in both the micro-creped and nonmicro-creped state. Among the three dressing types made from R/PET fabrics micro-creped with different patterns, the fabrics micro-creped with #2 ripple pattern show the most improvement in fluid transfer.

It is postulated that the decreased fluid transfer as the dressing weight increases is due to increased absorption by the dressing. As the dressing weight or fabric basis weight increases, the amount of fiber encountered by the fluid increases and the portion of fluid retained goes up also. The result is that a smaller amount of fluid is available to transfer through the primary dressing to the secondary dressing.

Other embodiments will be within the scope of the following claims. As used in the claims, the word "dressing" includes both dressings and sponges, and the phrase "fabric of hydro-entangled fibers" means a fabric produced by passing a loose layer of fibers through an entangler wherein the layer is treated with liquid jetted under pressure from one or more rows of small orifices thereby to convert the layer into a cohesive structure in which the fibers are locked into place by fiber interaction without the need for an adhesive binder or filament fusing.

What is claimed is:

1. A dressing comprising at least one layer of a textile-like nonwoven fabric of hydro-entangled fibers, said fabric layer being characterized in that:
    said fibers comprise a blend of fibers including a percentage of thermoplastic fibers; and,
    said fabric is compacted subsequent to hydro-entangling said fibers to rearrange said fabric layer into a series of wave-like undulations, whereby said fabric subsequent to and solely as a consequence of said compacting has an absorptive capacity and a liquid transfer both of which are greater than the absorptive capacity and liquid transfer of a hydro-entangled fabric layer of the same fabric weight and fiber blend that has not been compacted.

2. The dressing of claim 1 wherein said fibers comprise a blend including at least 15 percent thermoplastic fibers.

3. The dressing of claim 2 wherein said fibers comprise a blend including 15 to 60 percent thermoplastic fibers.

4. The dressing of claim 1 wherein said fibers comprise a blend of cellulosic fiber and a thermoplastic fiber.

5. The dressing of claim 4 wherein said cellulosic fiber is rayon and said thermoplastic fiber is selected from the group consisting of polyester and polypropylene fibers.

6. The dressing of claim 1 wherein said fabric prior to said compacting has a weight in the range of about 20 to about 60 grams per square yard.

7. The dressing of claim 1 wherein said compacting is micro-creping.

8. The dressing of claim 7 wherein said fabric is micro-compacted with an overfeed of not less than 10 percent.

9. The dressing of claim 8 wherein said overfeed is in the range of about 20 to about 30 percent.

10. The dressing of claim 9 wherein said overfeed is about 30 percent.

11. The dressing of claim 7 wherein during said compacting said fabric contacted with a surface having a temperature of not less than about 250 degrees F. whereby said temperature sets said thermoplastic fiber of said fabric for maintaining the compacted configuration of said fabric.

12. The dressing of claim 11 wherein said temperature is about 300 degrees F.

13. A dressing comprising at least one layer of a textile-like nonwoven fabric of essentially unbonded, hydro-entangled fibers, said fabric layer being characterized in that:

said fibers comprise a blend of fibers including not less than about 15 percent thermoplastic fibers, said fabric layer is micro-creped at an overfeed of not less than about 10 percent and at a microcreper drum temperature of not less than about 250 degrees F. subsequent to hydro-entangling said fibers to form said fabric, and said fabric prior to said micro-creping has a weight in the range of about 20 to about 60 grams per square yard, whereby said fabric layer subsequent to and solely as a consequence of said micro-creping has an absorptive capacity and a liquid transfer both of which are greater than the absorptive capacity and liquid transfer of a hydro-entangled fabric layer of the same weight and fiber blend that has not been micro-creped.

14. The dressing of claim 13 wherein said fabric comprises a blend of rayon fibers and fibers selected from the group consisting of polyethylene fibers and polyester fibers.

15. The dressing of claim 14 wherein said blend includes in the range of 40 to 85 percent said rayon fibers.

16. The dressing of claim 14 wherein said blend includes rayon fibers and polyester fibers, and said fabric is micro-creped at an overfeed in the range of about 20 to about 30 percent.

17. The dressing of claim 16 wherein said fabric is micro-creped using a microcreper having a groove micro-creping pattern.

18. The dressing of claim 13 wherein said temperature is about 300 degrees F.

* * * * *